United States Patent [19]

Schon et al.

[11] Patent Number: 4,981,477

[45] Date of Patent: Jan. 1, 1991

[54] CATHETER FOR INTRODUCTION INTO THE TRACHEA AND THE BRONCHIAL SYSTEM

[76] Inventors: Rudolf Schon, Am Kumpel 18; Christoph Schmidt, Ferdinandstr. 10; Jurgen Russ, Rosental 32, all of 5300 Bonn 1, Fed. Rep. of Germany

[21] Appl. No.: 336,432

[22] Filed: Apr. 11, 1989

[30] Foreign Application Priority Data

Apr. 16, 1988 [DE] Fed. Rep. of Germany ....... 3812754

[51] Int. Cl.$^5$ .............................................. A61M 5/00
[52] U.S. Cl. .................................... 604/264; 604/281
[58] Field of Search ............... 604/264, 265, 280, 281, 604/282, 19, 35, 73, 93, 275; 128/656, 658, 207.15, 207.14, 200.26

[56] References Cited

U.S. PATENT DOCUMENTS

| | | | |
|---|---|---|---|
| 3,363,629 | 8/1969 | Kuhn | 604/281 |
| 3,661,144 | 9/1972 | Jensen et al. | 604/264 |
| 4,027,659 | 7/1977 | Slingluff | 604/280 |
| 4,117,836 | 10/1978 | Erikson | 604/281 |
| 4,221,220 | 9/1980 | Hansen . | |
| 4,275,724 | 6/1981 | Behrstock | 604/281 |
| 4,469,483 | 9/1984 | Becker et al. | 604/280 |
| 4,551,140 | 11/1985 | Shinohara | 604/280 |
| 4,643,716 | 2/1987 | Drach | 604/281 |
| 4,671,291 | 6/1987 | Wilson | 604/280 |
| 4,716,896 | 1/1988 | Ackerman . | |
| 4,781,704 | 11/1988 | Potter | 604/264 |

FOREIGN PATENT DOCUMENTS

| | | |
|---|---|---|
| 1211360 | 2/1966 | Fed. Rep. of Germany . |
| 7035135 | 2/1971 | Fed. Rep. of Germany . |
| 2364119 | 8/1974 | Fed. Rep. of Germany . |
| 8310315 | 8/1986 | Fed. Rep. of Germany . |
| 3608943 | 4/1987 | Fed. Rep. of Germany . |
| 0273951 | 7/1927 | United Kingdom ................ 604/280 |

OTHER PUBLICATIONS

"Ureteral Catheters Nylon Woven", A.C.M.I. Catalogue 1960, pp. 34 & 35.

Primary Examiner—C. Fred Rosenbaum
Assistant Examiner—Kathleen A. Daley
Attorney, Agent, or Firm—Antonelli, Terry, Stout & Kraus

[57] ABSTRACT

A tubular flexible suction catheter for introduction into the trachea and the bronchial system, has at least one continuous lumen for suctioning fluids out of a lung and a distal end zone that is fashioned to be wavy in an approximately W-shape in the longitudinal extension of the suction catheter.

21 Claims, 5 Drawing Sheets

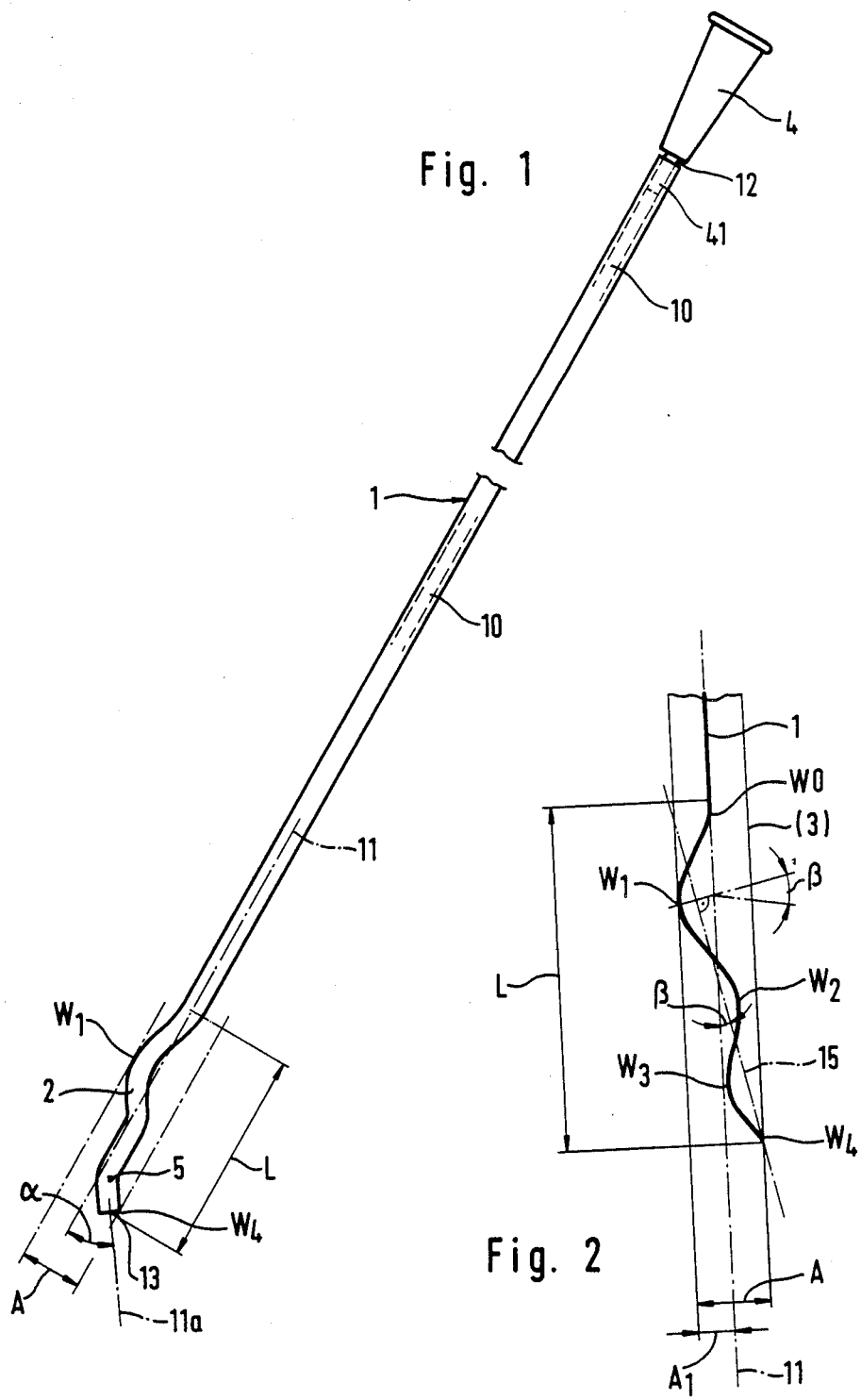

Fig. 8 "D-D"

CATHETER FOR INTRODUCTION INTO THE TRACHEA AND THE BRONCHIAL SYSTEM

This invention relates to a tubular flexible suction catheter for introduction into the trachea and the bronchial system and for suctioning fluids out of the lung, the catheter containing at least one lumen extending continuously from a proximal end to a distal end of the catheter.

Suction catheters of the type set forth above, are disclosed in DAS 2,364,119 and in German Pat. No. 3,608,943 there is disclosed a catheter with two continuously extending lumens, the first of which serves for suctioning and the second one serving for passing medicaments therethrough. Catheters for simultaneous aspiration and oxygenation, introduced into the trachea, are known, for example, from U.S. Pat. No. 4,300,550. An endotracheal resuscitation tube in which a permanent suction catheter is inserted is described in DOS 2,308,400.

In order to make introduction of an endotracheal tube into the larynx and the upper trachea possible without irritations and maximally painlessly, German Utility Model 70 35 135 has suggested to shape an elongated zone adjacent to the distal end of an endotracheal tube in an approximate S-configuration to simulate curvature of the patient's respiratory tract. Such an endotracheal tube, however, cannot be introduced all the way into the bronchi in order to effect direct suctioning at the lung.

DAS 1,211,360 also discloses a bronchial catheter with a tubular outer guide element of a rigid material, the distal end of which is bent by approximately 90° in adaptation to the respiratory tract so that it can be guided more easily past the larynx.

Suctioning of the tracheal and bronchial space must take place via the right as well as left lobes of the lung. However, on account of the somewhat unsymmetrical configuration of the bifurcation between the lobes, it happens under practical conditions that the flexible suction catheters, which are usually designed linear and tubular, are normally introduced during customary insertion through the trachea to an extend of up to 70% into the right lobe of the lung and the left lung lobe is reached at most to a degree of 30%. In order to overcome this troublesome situation, suction catheters are known which are bent twice at the end, but in each case by 90° mutually offset, in such a way that they form a three-dimensional hook; however, for each pulmonary lobe a separate suction catheter is required, bent in the corresponding two different directions and planes. This constitutes a considerable expense in treatment since, respectively, a separate suction catheter must be introduced for the right-hand suctioning of the lung and for the left-hand suctioning of the lung, and these suction catheters must not be confused with each other.

The invention is based on the object of providing a tubular flexible suction catheter for the bronchial system so that the same suction catheter can be introduced flawlessly and with a probability bordering on certainty in a predetermined way into the right pulmonary lobe or into the left pulmonary lobe.

This object has been attained according to this invention by fashioning a zone immediately adjacent to the distal end of the suction catheter in the longitudinal extension of the suction catheter to be wavy, namely in an approximate W-shape. This "distal end zone" of the suction catheter is undulated only in one plane so that the catheter thus comes into contact, in the manner of a spring when being introduced into the trachea or passed through a resuscitation tube, with the walls of the trachea, and respectively, of the resuscitation tube on one side with a wave crest and on the other side with the end, and in this way the distal end with the lumen outlet can be guided in a controlled fashion into one of the two forks of the pulmonary lobes past the bifurcation. Depending on the direction into which points the distal wavy end of the suction catheter is pointed, the latter is perforce introduced into the right or left lung lobe. The intention of introducing the suction catheter into the right lung lobe or into the left lung lobe can be realized by the attitude of the suction catheter and/or by turning same by 180°.

In case of the approximately W-shaped undulation of the distal end, the first wave loop and the free leg of the "W" can constitute the two mutually diametrically opposed support points or contact points of the suction catheter in the trachea whereby the definite guidance of the suction catheter into the pulmonary lobes is made possible. The flexible suction catheters of a synthetic resin or natural rubber or soft rubber, however, must not be too soft since in such a case they would no longer exhibit adequate stability and could readily buckle and/or would tend to twist.

The suction catheters to be introduced into the bronchi through the trachea normally have a length of about 30–55 cm. Suitably, the provision is made according to this invention that the distal end zone up to the distal end of the suction catheter is made of a wavy shape along a length of about 40–80 mm. Thereby, the forked region at the bifurcation is also perfectly bridged, and introduction of the distal end of the suction catheter into the desired lobe of the lung is promoted.

In a further embodiment of the invention, the provision is made that the undulation is damped toward the distal end. This means that the first wave crest extended from the longitudinal axis of the suction catheter has the largest amplitude, and the subsequent wave crests following in the direction of the distal end exhibit respectively decreasing amplitudes. An adequate guidance of the distal end and of the suction catheter is obtained by waves of the end zone already over at least one up to about two wavelengths. In order to obtain an improvement of the spring action and thus of the contact action and guidance of the distal end of the suction catheter during introduction through the trachea or a resuscitation tube, the provision is furthermore made that the longitudinal wave axis is slightly inclined with respect to the longitudinal axis of the suction catheter. This inclination can exhibit an angle "$\beta$" of about 10°–40°, preferably 15°–35°.

In correspondence with the geometry of the trachea and bronchi, suction catheters usually have an average outer diameter of about 3–10 mm and correspondingly an inner diameter of about 2 to 8 mm. Suitably, it is now proposed that the size of the maximum amplitude of the first wave crest corresponds approximately to the size of the average outer diameter of the suction catheter. In case of a very small outer diameter of the suction catheter, the amplitude can, however, also be larger than such diameter; this also holds true in case of the formation of only about one and one-half wave at the distal end of the suction catheter. The wave amplitudes of the end, extending out of the longitudinal axis of the suction catheter toward both directions, in total are not to exceed a value corresponding approximately to twice to three times the average outer diameter of the suction catheter. Such a suction catheter can also be introduced even through a resuscitation tube into the bronchi.

In a further development of the suction catheter according to the invention, the provision is made that the wavy distal end zone terminates with a wave leg that is deflected out of the longitudinal axis of the suction catheter at an acute angle "α" which can amount to about 10°–45°.

In order to avoid injuries to the mucosa, the suction catheter can be conventionally surrounded by an annular bead on the outside at the distal end. Likewise, one or several radial apertures can be arranged in the zone of the distal end, distributed over the circumference. Customarily, the outlet of the at least one lumen and the end cross section of the distal end extend approximately perpendicularly to the longitudinal axis of the suction catheter. On account of the wave shaped-configuration of the end according to this invention, this configuration no longer runs perpendicularly to the longitudinal axis of the suction catheter, due to the bent portion. If the suction catheter is to be utilized not only for suctioning but also for the introduction of medicaments, for example, in case of a twin-lumen design, then it may be advantageous to fashion the single-lumen or twin-lumen suction catheter according to this invention in such a way that the end cross section of the distal end extends perpendicularly to the longitudinal axis of the wave leg, i.e. is designed practically in an undercut fashion. This ensures the discharging of medicaments in a jet form in the direction of the longitudinal axis of the suction catheter into the ducts of the lung. The distal end of the suction catheter can also be fashioned to be rounded.

The suction catheter according to this invention is suitable for introduction into the right-hand side as well as into the left-hand side lung lobe. The procedure is such that, after introduction of the suction catheter into the right pulmonary lobe, for example, the catheter is subsequently partially retracted again up to the trachea, then turned about the longitudinal axis by 180°, and then reintroduced, but now passing into the left-hand pulmonary lobe. It is advantageous to mark the suction catheter along its entire length with a linear scale. In this way, it can be ensured that the removal of the suction catheter from a pulmonary lobe, necessary during a treatment in order to effect introduction into the other pulmonary lobe after rotation, can take place to the necessary extent, i.e. neither too much nor too little. Moreover, it is possible to equip the suction catheter with an X-ray contrast strip or the like extending over the entire length of the suction catheter.

In order to avoid adhesion of the suction catheter to the walls of the trachea or to a resuscitation tube, the suction catheter can exhibit a smooth outer skin and optionally also an additional slip coating, e.g. on silicone basis.

In accordance with a further suggestion advanced by this invention, the suction catheter is finely ribbed on the outside, i.e. provided with ribs extending in the longitudinal direction of the suction catheter. In this arrangement, many small ribs are preferred, small grooves extending therebetween. At least four, preferably six or more ribs having a height of about 100–700 μm are provided in uniform distribution over the outer circumference of the suction catheter. In this way, the contact surface of the suction catheter against the trachea and, respectively, on the inside of the resuscitation tube is reduced during introduction, in accordance with this invention; consequently, the friction surface becomes smaller, and the suction catheter slides more readily and more advantageously so that it is not twisted (rotated) during introduction into the trachea or into the resuscitation tube.

The arrangement according to this invention is suitable in its use for all types of suction catheters introduced into the trachea for treating the bronchial system, through the nose, the windpipe, as well as through the trachea, with and without a resuscitation tube. An approximate marking can be provided at the proximal end of the suction catheter for the right-hand or left-hand orientation of the suction catheter equipped according to this invention, for introduction into the right or left pulmonary lobe.

The suction catheter of this invention can be produced by extrusion of a tubular hollow synthetic resin profile with externally located ribs. This hollow plastic profile is stretched and then cut to size at predetermined lengths, or vice versa. In case of these tubular flexible suctions, corresponding to a suction catheter, the subsequent distal end zone must then be additionally corrugated to have the W-shape undulation. For this purpose, it is suggested to preform a supporting wire exhibiting the desired undulation and to introduce this preformed supporting wire into one end of the tubular section, the tubular section being in close contact with the supporting wire. Thereafter, the thus-preformed wavy section with the supporting wire is heated to the deformation temperature of the synthetic resin, between about 65° and 120° C., depending on the synthetic resin, and then quenched directly in a cold water bath. Thereafter, the supporting wire can be removed. To prevent the supporting wire from adhering to the section, the wire can be coated with a non-slip coating, for example "Teflon". It is also possible to insert the tubular flexible section in a bipartite mold corresponding to the outer contour of the suction catheter with a wavy distal end zone, and to heat the mold with the inserted section to an adequate shaping temperature for the synthetic resin and thereafter to quench the preformed section. In any event, a permanent deformation of the distal end zone of the suction catheter in the desired wavy configuration is achieved.

The invention will be described hereinafter with reference to like embodiments illustrated in the accompanying drawings wherein:

FIG. 1 shows a single-lumen suction catheter in a top view;

FIG. 2 shows a diagrammatic view of the configuration of the wavy distal end zone;

FIG. 8 is a cross section DD of the catheter shown in FIG. 7.

Figure 3:
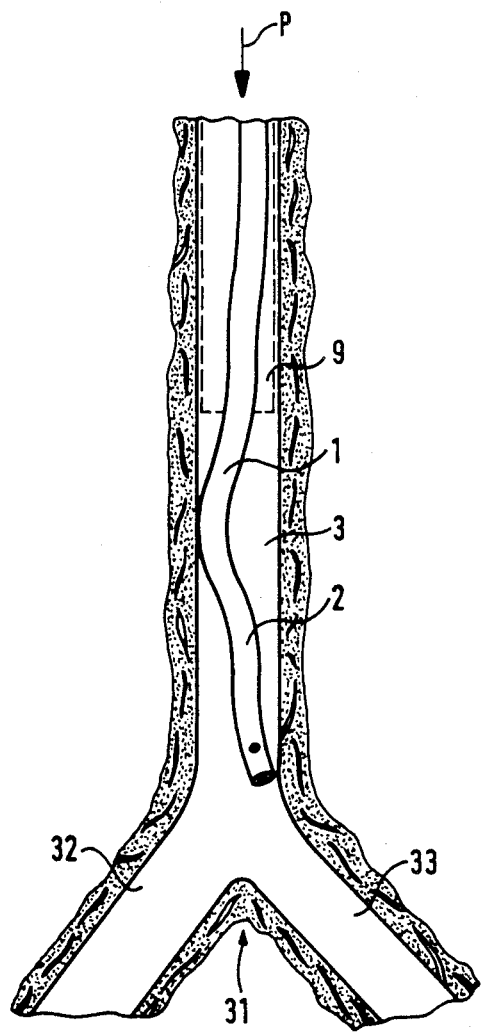
FIGS. 3 and 4 show schematic views of the introduction of the suction catheter into the pulmonary lobes.

The suction catheter according to FIG. 1 having a length of about 50 cm is produced from a flexible transparent thermoplastic synthetic resin by extrusion with subsequent stretching and plastic permanent deformation. The suction catheter 1 has a single lumen 10 for suctioning extending from the proximal end 12 to the distal end 13 with a lung outlet.

The diameter of lumen 10 is about three to four millimeters the corresponding outer diameter is about 4,5 to 7 mm. At the proximal end 12, the funnel 4 with the nipple 41 is inserted in the lumen entrance. It is also possible to mold the funnel 4 directly to the proximal end 12 of the suction catheter whereby the latter is provided with a conically flaring end. In the region of the distal end 13, radial openings 5 are usually provided in the suction catheter, distributed over the circumference and extending to the lumen; at least one opening is formed. The distal end can be surrounded with the annular bead 6 on the outside. The suction catheter 1 has a longitudinal axis 11. The distal end zone 2 is designed toward the end 13 to be wavy over the length L. Undulation extends in a single plane and has an approximately W-shaped configuration, the waviness running with attenuation toward the distal end 13, i.e. with a diminishing amplitude of the wave crests, see also FIG. 2. The embodiment shown in FIG. 1 is approximately actual size. The longitudinal axis 15 of the zone of undulation is slightly inclined at the angle "$\beta$" with respect to the longitudinal axis 11 of the suction catheter 1. This becomes possible, for example, by providing that the suction catheter at the beginning of the undulation is slightly deflected from the longitudinal axis 11 with a very small wave trough W0 and is then converted into the desired W-shape with the first large wave of maximum amplitude. The waving of the distal end zone is to be performed so that the contact point with the trachea and, respectively, the resuscitation tube can be obtained toward each side with respect to the longitudinal axis 11 of the suction catheter whereby the latter is introduced in a supported fashion so that it cannot buckle. In the illustrated embodiment according to FIGS. 1 and 2, these are the contact points W1 on the first maximum wave crest and on the opposite side the contact point W4, i.e. the end of the free leg of the last wave at the distal end. The trachea is indicated schematically in FIG. 2 by reference numeral 3.

Figure 6A:
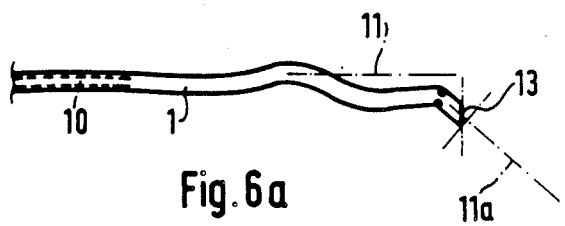
FIG. 6 shows in 6a, 6b and 6c suction catheters with differing distal end zones in fragmentary views.

Considering the usually predetermined outer diameters of the suction catheters, the maximum amplitude A1 should correspond approximately to an average outer diameter of the suction catheter. The sum total, namely the maximum sum A, of the wave deflections toward both sides of the longitudinal axis 11 of the suction catheter should not exceed three times the outer diameter of the suction catheter; preferably it should amount to only twice to two and a half times. The wavy end zone exhibits, in particular, three formed wave crests about the longitudinal wave axis 15, namely W1, W2, W3 according to FIG. 2. The end of the undulating W terminates in the open leg W4, the longitudinal axis 11a of which, see FIG. 1, is inclined under the angle "$\alpha$" with respect to the longitudinal axis 11 of the suction catheter. The lumen 10 has its outlet, in the illustrated embodiment according to FIG. 1, perpendicular to the leg axis 11a. However, it is also possible to fashion this outlet and/or the end cross section in such a way that, with a bend closely adjacent to the distal end, this outlet or end cross section still extends perpendicularly to the longitudinal axis 11 of the suction catheter. Examples are illustrated in the arrangements according to FIGS. 6a and 6c. In this case, the end cross section is undercut with a bevel at the distal end 13 with respect to the leg axis 11a, so that the lumen outlet extends approximately perpendicularly to the longitudinal axis 11 of the suction catheter and thus makes it possible to effect axial suctioning from the lung and, respectively, axial introduction of medicaments in a direction corresponding to the axis 11, in a corresponding way.

Figure 5:
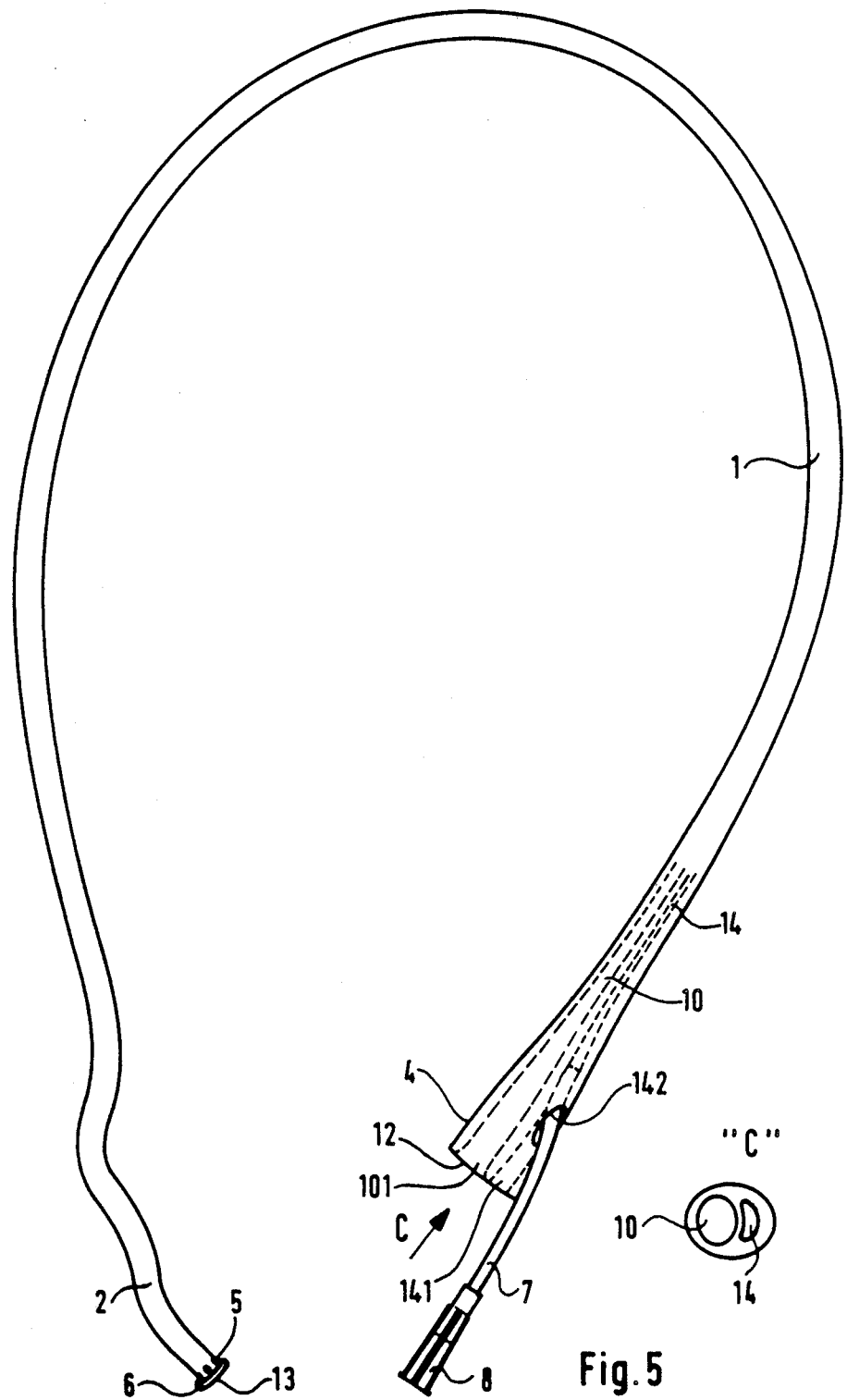
FIG. 5 shows a twin-lumen suction catheter in a top view.
Figure 6B:
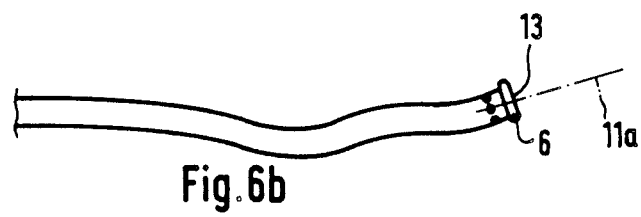
Figure 6C:
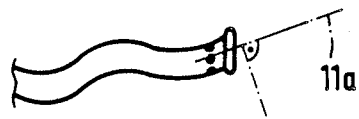

Also, in case of suction catheters where an annular bead 6 has been molded to the distal end, see fragmentary view of FIG. 6b, an end cross section extending perpendicularly to the longitudinal axis 11 of the suction catheter can be obtained by a corresponding beveling of the bent leg, see FIG. 6c. This is of importance if twin-lumen suction catheters are utilized wherein a medicament is to be inserted maximally deeply into the lung through a lumen. Such a twin-lumen suction catheter is illustrated in FIG. 5. This catheter is designed to include, additionally beside the lumen 10 for suctioning, a further lumen 14 for conducting medicaments extending continuously from the proximal end to the distal end. The lumen 14, however, exhibits a smaller cross section than the lumen 10. The lumen 14 has a diameter of about one to maximally two millimeters, whereas the lumen 10 has a diameter of about three to four millimeters. A hose 7 is inserted in the lumen 14 in the zone of the proximal end of the suction catheter through an opening 142 in the latter, an attachment 8 for a syringe being provided at the end of this hose. The lumens 10, 14 are conically widened with their inlets 101, 141 at the proximal end in order to be able to insert approximate connections. The lumen 14 terminates into the lumen 10 at the distal end 13 of the suction catheter 1 which is likewise equipped with the annular bead 6 and with radial apertures 5. The distal end zone 2 of the suction catheter 1 is undulated in a W-shape. The lumens 10, 14 are indicated only schematically.

Figure 4:
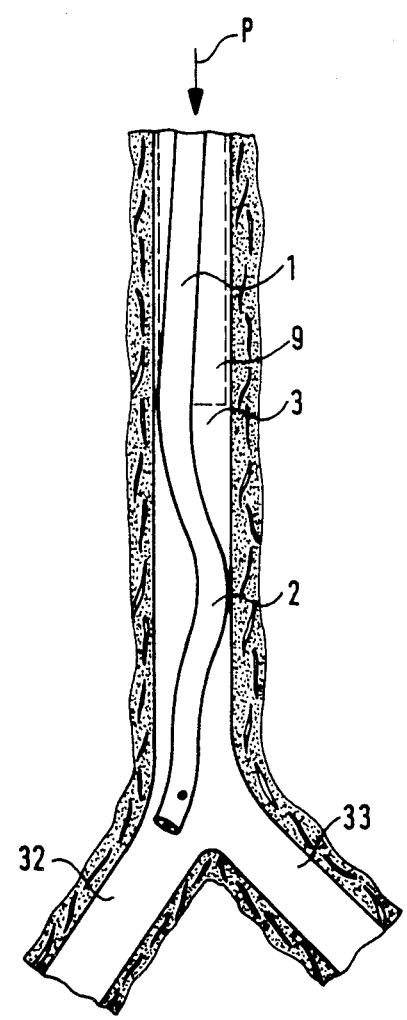

FIGS. 3 and 4 show the introduction of the suction catheter 1 according to this invention with the wavy distal end zone through the trachea 3 down into the pulmonary lobes 32, 33. In this arrangement, the resuscitation tube 9, indicated in dashed lines, is suitably provided in addition as an introduction aid in the upper trachea 3. At the end of the trachea, the paths above the bifurcation 31 divide into the right pulmonary lobe 32 and the left pulmonary lobe 33. Depending on the guidance and orientation of the suction catheter 1 with the wavy end zone 2, a positive introduction of the suction catheter takes place upon insertion in the direction of the arrow, according to FIG. 3 into the left pulmonary lobe 33 via the bifurcation, or into the right pulmonary lobe 32, according to FIG. 4. The positive guidance of the wavy distal zone 2 of the suction catheter along the walls, i.e. the mucous membranes, the trachea, and the resuscitation tube with the contact points can be seen from FIGS. 3 and 4. Introduction of the suction catheter 1 takes place in the direction of arrow P. By a simple rotation of the suction catheter 1 about its longitudinal axis by 180°, the same suction catheter can be utilized alternatingly for the secure insertion in the right or left pulmonary lobe.

Upon the insertion of the suction catheter first in one of the pulmonary lobes, the suction catheter can be pulled out in opposition to the direction of arrow P, after termination of the suction step, until the catheter is again completely within the trachea 3 with its distal end. Thereafter the suction catheter is turned by 180° into the other lobe of the lung.

Figure 7:
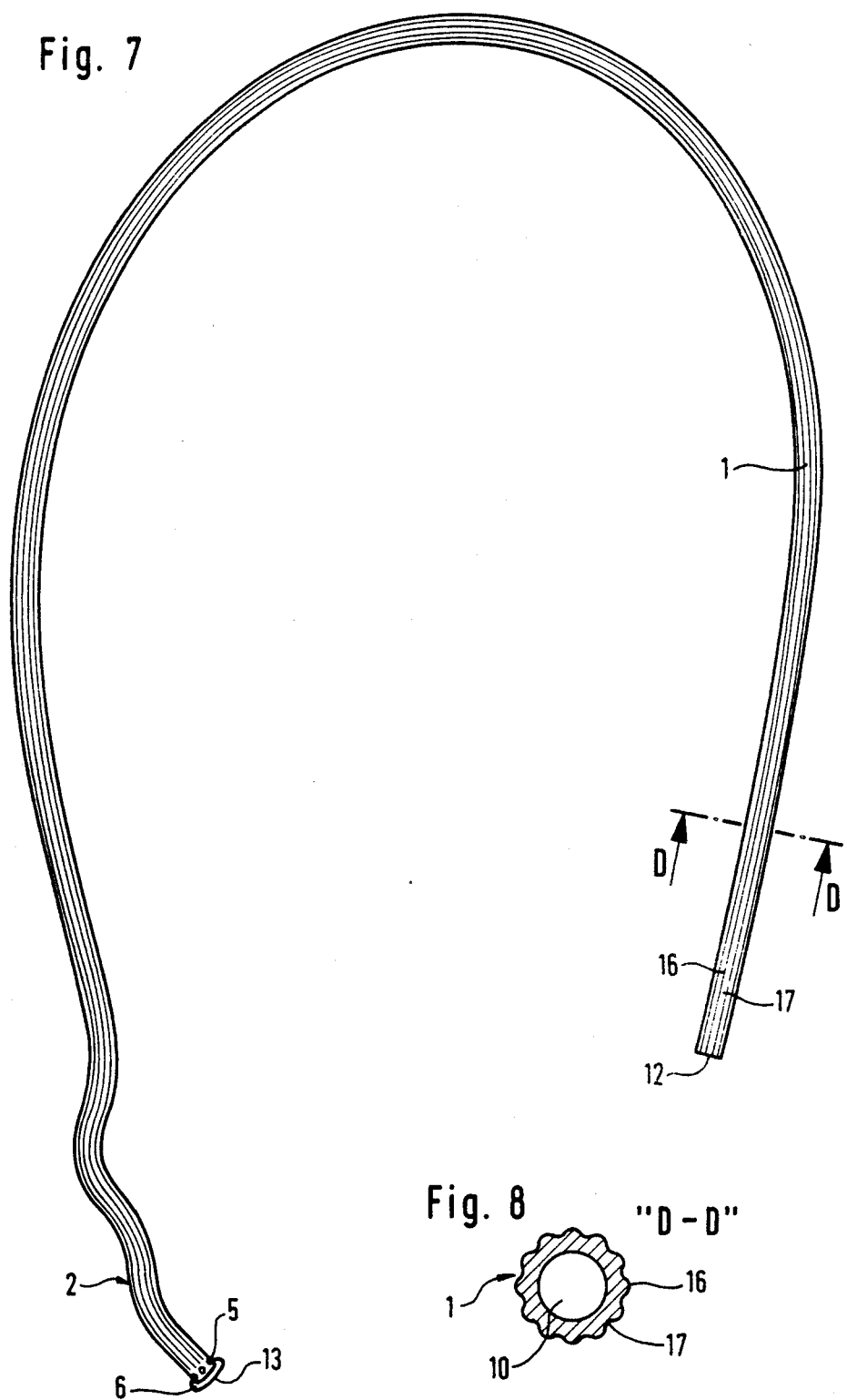
FIG. 7 is a top view of a ribbed suction catheter.

In order to reduce friction of the suction catheter during insertion through the resuscitation tube 9 and, respectively, the trachea 3, the suction catheter, see FIGS. 7 and 8, is suitably profiled on its surface. In this connection, ribs 16 and grooves 17 extending preferably in the longitudinal direction of the suction catheter are provided which are uniformly distributed over the circumference and run from the proximal end 12 to the distal end 13 or, respectively, to the annular bead 6 or the holes or radial openings 5. In case a connection member is to be applied from the outside to the proximal end 12 of the suction catheter, the ribs can be removed or leveled in this region.

FIG. 8 shows, in an enlarged view, a cross section through a ribbed suction catheter. Many fine ribs are uniformly provided, wherein the ribs have a height and, respectively, the grooves 17 have a depth of about 30 to 700 μm, depending on the diameter of the suction catheter.

In FIGS. 5 and 7 the catheter is shown in natural size, however according to its flexibility in a bent form. The distal end zone is preformed in W-shape which is relatively stiff and does not change its configuration.

We claim:

1. A tubular flexible bronchial suction catheter for introduction into the trachea and the bronchial system and for suctioning fluids out of the lung, said catheter having a proximal end and a distal end and containing at least one lumen extending continuously from the proximal end to the distal end, characterized in that said suction catheter has a longitudinal axis, a portion of the suction catheter is extended along said longitudinal axis and a distal end zone immediately adjacent to the distal end of the suction catheter is permanently undulated in one plane in a longitudinal extension of the suction catheter approximately in a W-shaped configuration, terminating with an open free wave leg that is inclined with respect to the longitudinal axis of the suction catheter.

2. A suction catheter according to claim 1, characterized in that the distal end zone is fashioned to be undulated with oppositely directed wave crests along a length of about 40–80 mm and the suction catheter has a length ranging from 30 to 55 cm.

3. A suction catheter according to claim 2, characterized in that wave crests of the undulated distal end zone extend toward the distal end in a damped fashion.

4. A suction catheter according to claim 2, characterized in that the size of the maximum amplitude (A1) of a first wave crest of waves at the distal end zone corresponds approximately to the size of average outer diameter of the suction catheter.

5. A suction catheter according to claim 1, characterized in that wave crests of the undulated distal end zone extend toward the distal end in a damped fashion.

6. A suction catheter according to claim 1, characterized in that the undulated distal end zone extends over at least one and a half up to about two wavelengths of initially formed wave in the undulated distal end zone.

7. A suction catheter according to claim 1, characterized in that a longitudinal wave axis of waves formed at the distal end zone is slightly inclined with respect to the longitudinal axis of the suction catheter.

8. A suction catheter according to claim 7, characterized in that the longitudinal wave axis of the waves of the distal end zone is inclined by an angle "β" of about 10 to 40 degrees with respect to the longitudinal axis of the suction catheter.

9. A suction catheter according to claim 1, characterized in that the catheter exhibits an average outer diameter of about three to ten millimeters and an inner diameter of about 2 to 8 millimeters.

10. A suction catheter according to claim 1, characterized in that the distal end is formed by the open free wave leg which is in a last wave of the W-shaped configuration and which is deflected under an acute angle "α" with respect to the longitudinal axis of the suction catheter.

11. A suction catheter according to claim 10, characterized in that the angle "α" has the value of about 10° to 46°.

12. A suction catheter according to claim 1, characterized in that wave deflections of the undulated distal end zone from the longitudinal axis of the suction catheter do not exceed in total value (A) corresponding approximately to the size of from twice to maximally three times the average outer diameter of the suction catheter.

13. A suction catheter according to claim 1, characterized in that the distal end is surrounded by an annular bead on the outside.

14. A suction catheter according to claim 1, characterized in that a surface surrounding an outlet at the distal end extends approximately perpendicular to the longitudinal axis of the suction catheter.

15. A suction catheter according to claim 1, characterized in that the catheter is marked on the outside with a linear scale.

16. A suction catheter according to claim 1, characterized in that the catheter is equipped with an X-ray contrast strip or the like, extending in the longitudinal direction of the suction catheter from the distal end to the proximal end.

17. A suction catheter according to claim 1, characterized in that the catheter is provided on the outside with ribs extending in the longitudinal direction of the suction catheter.

18. A suction catheter according to claim 17, characterized in that at least four, preferably six or more ribs of a height of about 30–700 μm are arranged in uniform distribution over the circumference of the suction catheter.

19. A suction catheter according to claim 1, characterized in that the undulated distal end zone having the W-shaped configuration includes at least one portion that extends across a longitudinal extension of the longitudinal axis of the suction catheter.

20. A suction catheter according to claim 1, characterized in that the undulated distal end zone has at least one wave crest extending on one side of a longitudinal extension of the longitudinal axis of the suction catheter and at least another wave crest extending on the other side of the extension of the longitudinal axis of the suction catheter.

21. A suction catheter according to claim 1, characterized in that the portion of the suction catheter extended along said longitudinal axis extends from said proximal end to the distal end zone.

* * * * *